US007608612B2

(12) United States Patent
Matthews et al.

(10) Patent No.: US 7,608,612 B2
(45) Date of Patent: Oct. 27, 2009

(54) RADIOSENSITIZER FORMULATIONS AND METHODS FOR USE

(75) Inventors: Richard H. Matthews, 700 Winding Ride Rd., Jackson, MO (US) 63755; Nuran Ercal, Rolla, MO (US); Robert Zand, Ann Arbor, MI (US)

(73) Assignee: Richard H. Matthews, Jackson, MO (US)

( * ) Notice: Subject to any disclaimer, the term of this patent is extended or adjusted under 35 U.S.C. 154(b) by 280 days.

(21) Appl. No.: 11/336,419

(22) Filed: Jan. 20, 2006

(65) Prior Publication Data

US 2006/0193917 A1 Aug. 31, 2006

Related U.S. Application Data

(60) Provisional application No. 60/681,597, filed on May 17, 2005, provisional application No. 60/645,630, filed on Jan. 21, 2005.

(51) Int. Cl.
*A61K 31/33* (2006.01)
*A01N 43/00* (2006.01)
(52) U.S. Cl. .................. 514/183; 514/94; 548/335.1
(58) Field of Classification Search .................. None
See application file for complete search history.

(56) References Cited

U.S. PATENT DOCUMENTS

| | | | |
|---|---|---|---|
| 4,241,060 A | 12/1980 | Smithen | 424/248.57 |
| 4,371,540 A | 2/1983 | Lee et al. | 424/273 R |
| 4,859,763 A | 8/1989 | Takayanagi et al. | 528/357 |
| 5,270,330 A | 12/1993 | Suzuki et al. | 514/398 |
| 5,532,380 A | 7/1996 | Suzuki et al. | 548/327.5 |
| 5,637,568 A | 6/1997 | Orsolini et al. | 514/15 |
| 5,733,566 A | 3/1998 | Lewis | 424/426 |
| 5,792,477 A | 8/1998 | Rickey et al. | 424/501 |
| 6,166,173 A | 12/2000 | Mao et al. | 528/398 |
| 6,180,116 B1 * | 1/2001 | Philippe et al. | 424/400 |
| 6,201,072 B1 | 3/2001 | Rathi et al. | 525/415 |
| 6,376,644 B1 | 4/2002 | Mao et al. | 528/398 |
| 6,699,504 B2 | 3/2004 | Rowe et al. | 424/486 |

FOREIGN PATENT DOCUMENTS

| | | |
|---|---|---|
| EP | 0 302 416 | 2/1989 |
| WO | WO 02/30472 | 4/2002 |

OTHER PUBLICATIONS

Chang et al 'Radiotherapy and Radiosensitizers in the Treatment of Glioblastoma Multiforme' Clinical Advances in Hematology and Oncology, 5(11), p. 894-902 and 907-915, 2007.*
Bruce, J., "Glioblastoma Multiforme," *eMedicine*, www.emedicine.com/med/topic2692.html; Jan. 13, 2005, pp. 1-20.
Char, D., et al., "Analysis of Melanoma Cell Type in Uveal Melanoma Following Treatment Failure," *Am. J. of Ophthalmology*, Oct. 2004, pp. 543- 546.
Fiets, W.E., et al., "Acute Toxicity of Concurrent Adjuvant Radiotherapy and Chemotherapy (CMF or AC) in Breast Cancer Patients: A Prospective, Comparative, Non-Randomised Study," *European Journal of Cancer*, 39, 2003, pp. 1081-1088.
Hurria, A., et al., "Management of Lung Cancer in Older Adults," *CA Cancer J. Clin.*, 2003, vol. 53, No. 6, pp. 325-341.
Keilholz, U., et al., "A Clinical Phase I Trial of Gemcitabine and Treosulfan in Uveal Melanoma and Other Solid Tumours," *European Journal of Cancer*, vol. 40, 2004, p. 2047-2052.
Lau, W.Y., "Primary Liver Tumors," *Seminars in Surgical Oncology*, 2000, vol. 19, pp. 135-144.
Li, Y., et al., "Treatment of Intracranial Rat Glioma Model with Implant of Radiosensitizer and Biomodulator Drug Combined with External Beam Radiotherapy," *Int. J. Radiation Oncology Biol. Phys.*, vol. 58, No. 2, pp. 519- 527, 2004.
Nagarajan, K., et al., "Nitroimidazoles: Part XIX—Structure-Activity Relationships," Indian Journal of Chemistry, Section B, vol. 23B, No. 4, Apr. 1984, pp. 342-362.
Malone, J., et al., "Disease Control, Survival, and Functional Outcome After Multimodal Treatment for Advanced-Stage Tongue Base Cancer," *Head and Neck*, Jul. 2004, pp. 561-572.
Matthews, R., "Nitrohistidine; a Radiosensitizer Concentrated by Cancer Cells," Advances in Cancer Research; 2004, p. B95, Abstract.
Martinez, A., et al., "Improvement in Dose Escalation Using the Process of Adaptive Radiotherapy Combined with Three-Dimensional Conformal or Intensity-Modulated Beams for Prostate Cancer," *Int. J. Radiation Oncology Biol. Phys.*, vol. 50, No. 5, 2001, pp. 1226-1234.
Pawlik, T., et al., "Malignant Melanoma: Current State of Primary and Adjuvant Treatment," *Critical Reviews in Oncology/Hematology*, vol. 45, 2003, pp. 245-264.
Reynolds, P, et al., "Treatment of Skin Malignancies," *The Journal of Family Practice*, vol. 52, No. 6, Jun. 2003, pp. 456-458.
Seidenfeld, J., et al., "Radiofrequency Ablation of Unresectable Primary Liver Cancer," *J. Am. Coll. Surg.*, 2002, pp. 813-828.
Tautz, W., et al., "Nitrohistidines and Nitrohistamines," Journal of Medicinal Chemistry, Jun. 1973, vol. 16, No. 6, pp. 705-707.
Trout, G., "Synthesis of Some Histidine Analogs and Their Effects on the Growth of a Histidine-Requiring Mutant of Leuconostoc Mesenteroides," Journal of Medicinal Chemistry, vol. 15, No. 12, 1972, pp. 1259-1261.

* cited by examiner

*Primary Examiner*—Patricia A Duffy
*Assistant Examiner*—Christopher R Stone
(74) *Attorney, Agent, or Firm*—Sunstein Kann Murphy & Timbers LLP

(57) ABSTRACT

The present invention provides radiosensitizer compositions, in controlled-release formulations or other acceptable formulations, particularly nitrohistidine radiosensitizer compositions, which may be administered by any suitable means including oral, intravenous, arterial infusion, intraperitoneal, intramuscular, subcutaneous, surgical, and topical. Optionally, radiosensitizer compositions may be formulated with other agents, including chemotherapy agents and agents that provide a synergistic radiosensitizing effect. Methods of potentiating radiotherapy cancer treatment of cancers in humans, particularly of astrocytomas, are also presented, wherein a radiosensitizer composition is administered and radiotherapy is directed to the site of the tumor. Chemotherapy regimens may also be used as adjuvant therapy.

4 Claims, 5 Drawing Sheets

Metronidazole
(Flagyl)

Misonidazole

RO-07-0554

RO-11-3696

SR-2508
(Etanidazole)

RO-03-8799
Pimonidazole

RSU-1069

RADIOSENSITIZER FORMULATIONS AND METHODS FOR USE

CROSS REFERENCE TO RELATED APPLICATIONS

The present application is a regular utility application which claims priority from two provisional patent applications, U.S. Application Ser. No. 60/645,630 filed Jan. 21, 2005 and U.S. Application Ser. No. 60/681,597 filed May 17, 2005, both of which are hereby incorporated by reference herein.

TECHNICAL FIELD AND BACKGROUND ART

The present invention relates to histidine derivatives for use as a radiosensitizer in the treatment of cancers including lung carcinomas, breast cancers, prostate cancers, cancers of the cervix and endometrium, neuroblastomas, lymphomas, gliomas, melanomas, squamous cell carcinomas, sarcomas, adenocarcinomas, astrocytomas, head-and-neck tumors, and GI tumors. More particularly, the invention relates to nitrohistidine, alone or in combination with other agents, prepared in slow-release formulations or normal release formulations, for the treatment of the brain tumor glioblastoma multiforme.

Histidine is one of 20 naturally occurring amino acids serving as subunits for proteins. It is often present at the catalytic active site of enzymes. Histidine is one of the nutritionally essential amino acids for mammalian cells, meaning that it cannot be synthesized by mammals, so it must be ingested and then taken up by cells to sustain protein synthesis. Rapidly-growing cells and tissues must be effective at taking up histidine from the environment, and cancer cells, in particular, usually have several very effective amino acid transport systems to aid them in competing for amino acids with other cells and tissues. Previous studies of the active transport of histidine in murine ascites tumor cells (1, 2, 3) indicate that there are two major amino acid transport systems for the uptake of histidine, and most cancer cells necessarily have both systems to permit their continued and rapid growth.

Previous studies have also indicated that nitroimidazoles have some capacity to act as radiosensitizers. Examples include metronidazole (Flagyl), misonidazole, RO-07-0554, RO-11-3696, RO-03-8799 (Pimonidazole), SR-2508 (Etanidazole) and RSU-1069, shown in FIG. 1. These compounds are sometimes referred to as "true radiosensitizers" in that they can apparently substitute for oxygen in "fixing" radiation-induced damage of DNA, making it non-reversible and lethal.

Hypoxic cells are difficult to kill with ionizing radiation compared to normal cells because ionizing radiation requires oxygen to "fix" a lesion transiently induced in DNA by the ionizing radiation in order to kill the cell, and hypoxic cells have little to no oxygen exposure, particularly deep within a tumor. Various attempts to overcome the problem of killing hypoxic cells have been made over the past years. Administration of hyperbaric oxygen or carbogen (a mixture of oxygen and carbon dioxide) has proved problematic, even dangerous, in clinical application, and resulted in mixed results.

A limitation of the nitroimidazole radiosensitizers is that although a number have been found to be effective radiosensitizers in vitro, they have limited practical effectiveness in vivo because they are not concentrated by cancers. Only 5 of 38 clinical trials for the most extensively studied of the nitroimidazoles, misonidazole, suggested any clinical benefit for misonidazole as a radiosensitizer, probably because the compound exhibits poor concentration in tumors.

SUMMARY OF THE INVENTION

In a first embodiment of the invention there is provided a radiosensitizer composition comprising an effective amount of a nitrohistidine, represented by any of formulas (I) or (II):

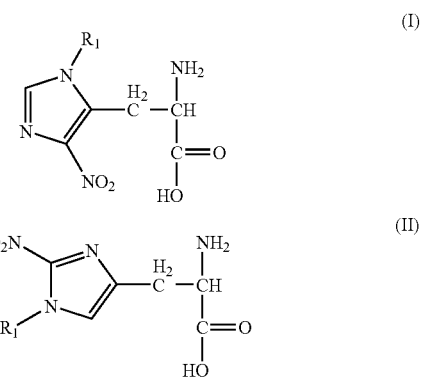

wherein $R_1$ is H or alkyl.

The radiosensitizer of formula (I) or (II) may be racemic or substantially optically pure. Thus, the radiosensitizer of formula (I) may be a racemic 4(5)-nitrohistidine or may be a substantially optically pure 4(5)-nitro-L-histidine. Likewise, the radiosensitizer of formula (II) may be a racemic 2-nitrohistidine or may be a substantially optically pure 2-nitro-L-histidine. In other embodiments, the radiosensitizers of formulas (I) and (II) may optionally comprise one or more agents. These other agents may be buthionine sulfoximine, which is an inhibitor of glutathione, N-(phosphonacetyl)-L-aspartic acid (PALA), which is an inhibitor of L-aspartate transcarbamylase, a chemotherapeutic agent, or any combination thereof.

In some embodiments, the chemotherapeutic agent is a nitrosourea agent, cisplatin, carboplatin (CBDCA), bleomycin, doxorubicin, methotrexate, cyclophosphamide, gemcitabine, treosulfan, 5-fluorouracil, dacarbazine, temozolomide, 9-nitrocamptothecin, vincristine, fotemustine, lomustine, a cytokine, an interferon, or any combination thereof Other embodiments in accordance with the present invention provide a radiosensitizer composition as described above, further comprising a biomodulator compound. The biomodulator compound may be a controlled-release compound, such as a slow-release compound, and may be a biodegradable polymer. In specific embodiments, the biodegradable polymer is selected from the group consisting of a homopolymer of lactic acid; a homopolymer of glycolic acid; a copolymer of poly-D,L-lactic acid and glycolic acid; a water-insoluble peptide salt of a luteinizing hormone-releasing hormone (LHRH) analogue; a poly(phosphoester); a bis(p-carboxyphenoxy) propane (CPP) with sebacic acid copolymer; a polyanhydrides polymer; poly(lactide)-co-glycolide)polyethylene glycol copolymers; and an ethylene-vinyl acetate copolymer.

Another embodiment provides a method of potentiating radiotherapy cancer treatment comprising administering to a patient in need thereof a therapeutically effective amount of a composition comprising a radiosensitizer of formula (I) or (II):

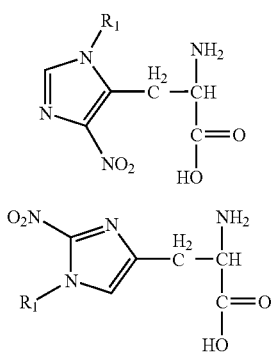

wherein $R_1$ is H or alkyl, and directing radiotherapy at a prescribed dosage to a tumor. Still another embodiment provides a method of potentiating radiotherapy cancer treatment by administering an effective amount of a composition comprising a radiosensitizer of formula (I) or (II), wherein the composition further comprises one or more agents, and the agents may be buthionine sulfoximine, a nitrosourea agent, N-(phosphonylacetyl)-L-aspartic acid (PALA), a chemotherapeutic agent, or any combination thereof. In particular embodiments of the method for potentiating radiotherapy cancer treatment, the chemotherapeutic agent is a nitrosourea agent, cisplatin, carboplatin (CBDCA), bleomycin, doxorubicin, methotrexate, cyclophosphamide, gemcitabine, treosulfan, 5-fluorouracil, dacarbazine, temozolomide, 9-nitrocamptothecin, vincristine, fotemustine, lomustine, a cytokine, an interferon, or any combination thereof. Alternatively, specific embodiments provide a method of potentiating radiotherapy cancer treatment as described, further comprising administering chemotherapy after directing radiotherapy. In some embodiments, the method further comprises administering chemotherapy by administering a nitrosourea agent, cisplatin, carboplatin (CBDCA), bleomycin, doxorubicin, methotrexate, cyclophosphamide, gemcitabine, treosulfan, 5-fluorouracil, dacarbazine, temozolomide, 9-nitrocamptothecin, vincristine, fotemustine, lomustine, a cytokine, an interferon, or any combination thereof.

In other specific embodiments, there is provided a method of potentiating radiotherapy cancer treatment by administering an effective amount of a radiosensitizer composition of formula (I) or (II) and directing radiotherapy at a prescribed dosage to a locus of cancer, wherein the method also comprises administering chemotherapy before directing radiotherapy. In some embodiments, administering chemotherapy before directing radiotherapy includes administering a nitrosourea agent, cisplatin, carboplatin (CBDCA), bleomycin, doxorubicin, methotrexate, cyclophosphamide, gemcitabine, treosulfan, 5-fluorouracil, dacarbazine, temozolomide, 9-nitrocamptothecin, vincristine, fotemustine, lomustine, a cytokine, an interferon, or any combination thereof.

Alternative embodiments provide a method of potentiating radiotherapy cancer treatment as described, further comprising, in administering, providing the composition in a slow-release formulation, and alternatively, wherein the slow-release formulation is administered by any suitable means including oral, intravenous, arterial infusion, intraperitoneal, intramuscular, subcutaneous, surgical, and topical.

In accordance with particular embodiments of these methods, the slow-release formulation comprises a biodegradable polymer, and the biodegradable polymer is selected from the group consisting of a homopolymer of lactic acid; a homopolymer of glycolic acid; a copolymer of poly-D,L,-lactic acid and glycolic acid; a water-insoluble peptide salt of a luteinizing hormone-releasing hormone (LHRH) analogue; a poly(phosphoester); a bis(p-carboxyphenoxy)propane (CPP) with sebacic acid copolymer; a polyanhydrides polymer; poly(lactide)-co-glycolide)polyethylene glycol copolymers; and an ethylene-vinyl acetate copolymer.

In some specific embodiments of the method, the slow-release formulation releases the radiosensitizer over a period of four or more weeks, alternatively over a period of one week or more, or alternatively over a period of 24 hours or more. The cancers to be treated include any of a brain cancer, a lung cancer, a head-and-neck cancer, a GI cancer, a breast cancer, a prostate cancer, a lymphoma, a sarcoma, a melanoma, a cancer of the cervix or endometrium, a bladder cancer, a renal cancer, a liver cancer, or an ocular cancer. In a particular embodiment, the brain cancer is an astrocytoma, and more particularly, is glioblastoma multiforme; the lung cancer is either a small cell lung carcinoma or a non small cell lung carcinoma; and the head-and-neck cancer is squamous cell carcinoma or adenocarcinoma.

More particular embodiments of the method of potentiating radiotherapy cancer treatment further comprise administering daily doses of the radiosensitizer throughout the course of treatment as an alternative to administering the radiosensitizer in a slow-release formulation.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
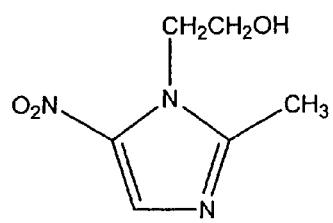
FIG. 1 shows prior art compounds categorized as nitroimidazole radiosensitizers.
Figure 1:
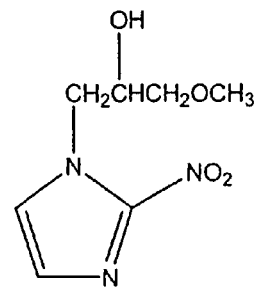
Figure 1:
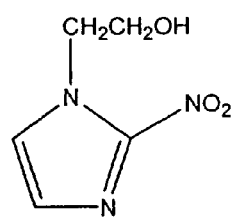
Figure 1:
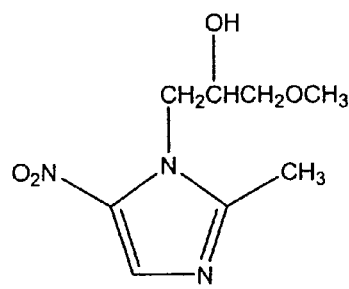
Figure 1:
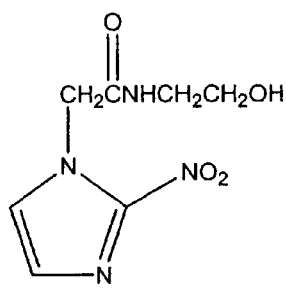
Figure 1:
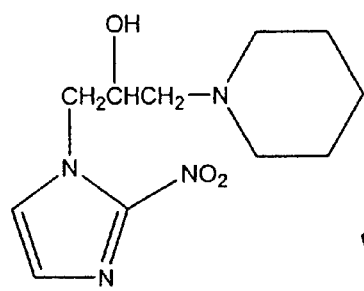
Figure 1:
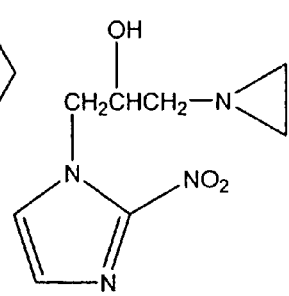

Definitions. As used in this description and the accompanying claims, the following terms shall have the meanings indicated, unless the context otherwise requires:

"Potentiate" means, in the context of this application to enhance or increase the effect of, for example, a drug, or to promote or strengthen, for example, a biochemical or physiological action or effect.

"Synergism" means, in the context of this application, increased activity with the two or more compounds over what is observed with either compound individually and what would be observed if the activities were merely additive.

"Slow-release compound" means, in the context of this application, a compound that, in conjunction with an active ingredient, releases the active ingredient to the surroundings in a controlled, non-instant manner, time-dependent manner. The slow release of the active agent over time may mean release over several hours, release over several days, or release over several weeks or longer.

"Biomodulator" means, in the context of this application, a compound or agent that is capable of modulating the release of a drug, or the activity of a drug action, by either increasing or decreasing activity of the drug or radiosensitizer, or increasing or decreasing the release of the drug to a desired location.

"Biodegradable polymer" means, in the context of this application, a polymer that can be degraded and metabolized by existing enzymes in the organism to which the biodegradable biopolymer is administered, with little or no side effects or toxicity.

Given the limited ability of ionizing radiation to kill hypoxic cancer cells because of the need for oxygen to "fix" the lesions in the DNA to make them lethal, a radiosensitizer capable of overcoming hypoxic resistance that is well-concentrated by cancer cells, that can be delivered to the tumor cells and released over time, and that has limited to no toxic side effects would be desirable, to augment radiation therapy.

Although 4(5)-nitrohistidine and substantially pure 4(5)-nitro-L-histidine (L-α-amino-β-[4(5)-nitro-4(5)-imidazolyl]propionic acid monohydrate) were previously synthesized (see Trout and Brossi et al., respectively), and an N-methyl 2-nitrohistidine (α-amino-β-(1-methyl-2-nitro-4-imidazolyl)propionic acid monohydrate) was also previously synthesized (see Brossi et al.), the researchers focused on the structural importance of histidine in determining its biological function (i.e., in protein synthesis—Trout) and on the efficacy of nitrohistidine as an anti-protozoal agent relative to the known anti-protozoal nitroimidazole agents, which turned out to be zero (Brossi et al.). Nitrohistidine has not been explored previously as a radiosensitizer.

Because histidine is an essential amino acid, and taken up in rapidly growing cells, it was hypothesized that nitrohistidine may likewise be taken up by rapidly growing cells, and that it may also act as a radiosensitizer, given its structural similarities to nitroimidazoles. Therefore, using the synthetic routes previously published by Trout and Brossi et al. (Trout, *J Med Chem* (1972) 15:1259-1262; and Brossi et al., *J Med Chem* (1973) 16: 705-707, both of which are incorporated by reference herein), 4(5)-nitrohistidine and substantially optically pure 4(5)-nitro-L-histidine were synthesized and used in studies developed to assess radiosensitizer capability and efficiency.

The two neutral amino acid transport systems that transport histidine into cells that have been studied in animal model tumor systems such as in Ehrlich ascites cells or S37 cells have points of interaction with amino acids in general that include the amino group, the carboxyl group, and the side chain. The nature of the side chain affects which of the two transport systems a substrate neutral amino acid will utilize, but more variability is allowed at the side chain point of interaction than at the amino and carboxyl points of interaction.

The best treatment for patients with refractive tumors such as lung tumors, head-and-neck tumors, GI tumors, and inoperable brain tumors like recurrent high-grade gliomas, including anaplastic astrocytoma and glioblastoma multiforme, often remains open to debate, and has not significantly increased the survival rate of patients with some of the worst tumors for the past 25 years, in spite of advances in surgery techniques, chemotherapy treatments, and radiotherapy and imaging techniques. Radiosensitizers have been utilized to increase the response of patients to radiotherapy, with dubious success reported using halogenated pyrimidine analogs such as bromodeoxyuridine (BrdUrd) and iododeoxyuridine (IdUrd) when treating patients with high-grade gliomas. Somewhat better success has been shown using such radiosensitizers for treatment of GI and head-and-neck tumors, promising greater enhancement with other tumors, given the right conditions.

In particular, the use of slow-release devices and slow-release or controlled-release formulations for combined delivery of the radiosensitizer with a biodegradable polymer capable of modulating delivery of the radiosensitizer at the locus of the tumor, or able to modulate delivery of a radiosensitizer that concentrates at a tumor site, have begun to be investigated. Such delivery means, coupled with an effective radiosensitizer that concentrates in tumor cells or can be delivered to the tumor location, represents a welcome chance to make significant advances in the war against the most deadly tumors. Recently, successful reports for treating an intracranial rat glioma model implanted with a radiosensitizer and biomodulator drug coupled with radiotherapy, proved effective at treating such cancers (see *Int J Radiat Oncol Biol Phys* (2004) 58: 519-527, incorporated by reference herein), statistically increasing the 180-day survival of rats with C6 tumor to 83% when the radiosensitizer was delivered using a biomodulator intracranial implant.

Astrocytomas are tumors that arise from astrocytes cells, part of the supportive, neuroglial tissue of the brain. Astrocytomas account for about half of all primary tumors of the brain and spinal cord. Glioblastomas are fast growing astrocytomas that contain areas of dead tumor cells (necrosis). Glioblastoma multiforme (GBM), the most common type of grade IV tumor, is also the most malignant and tends to invade adjacent brain tissue and spread throughout the central nervous system. Variants of GBM include gliosarcomas and giant cell glioblastomas.

Glioblastomas occur most often in the cerebrum, especially in the frontal and temporal lobes of the brain and represent about 30% of all primary brain tumors and about 50% of the astrocytomas. Glioblastoma is more common in older adults and affects more men that women. They are very difficult to treat and no significant advancements in their treatment have occurred in the past 25 years. Without therapy, patients with GBM uniformly die within 3 months. Patients treated with optimal therapy—to day this includes surgical resection, radiation therapy, and chemotherapy, have a median survival of approximately one year.

Uveal melanoma is the most common primary intraocular malignant tumor. Despite the ability to make an accurate diagnosis and availability of various primary treatments, mortality from this disease has remained unchanged for a number of reasons, primarily because of hematogenous metastases, mainly to the liver, which are often highly resistant to chemotherapy. Moreover, evidence suggests that if local treatment of the uveal melanoma fails, there is an increased incidence of metastases. Median survival times of between 5 and 7 months are not uncommon after chemotherapy of metastasized uveal melanoma.

EXAMPLE 1

In Vitro Study of 4(5)-Nitrohistidine as a Radiosensitizer

Figure 2A:
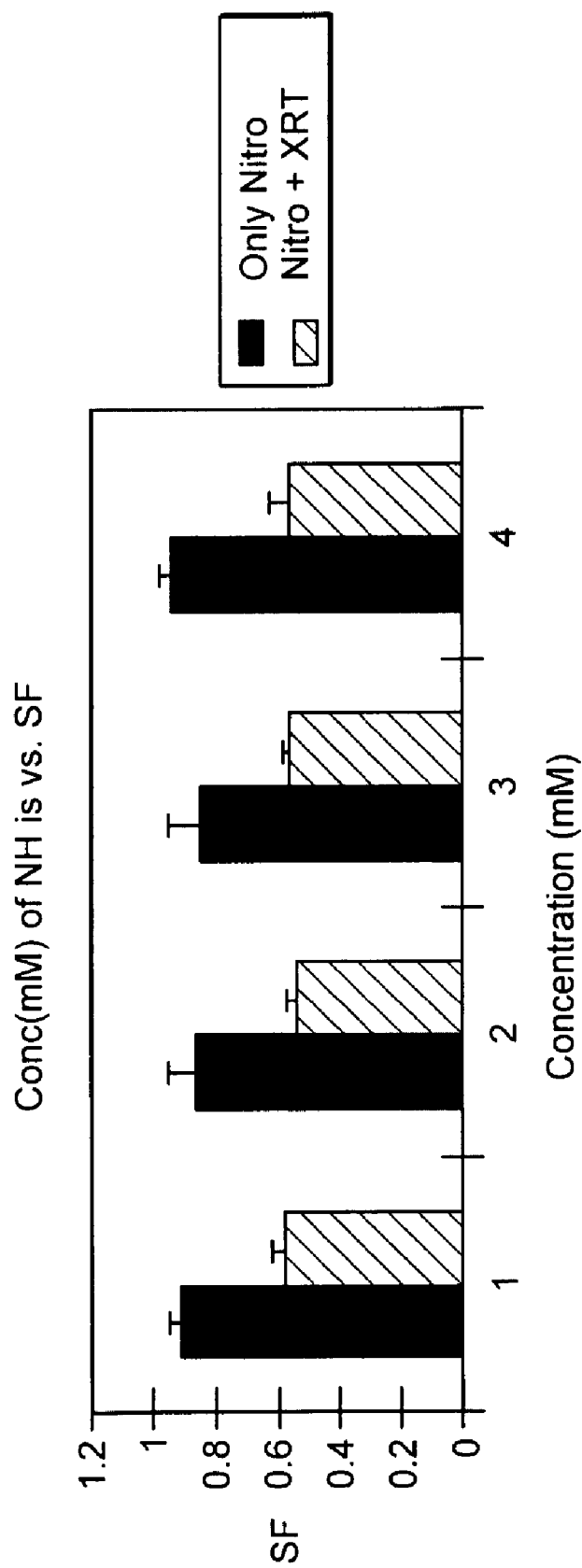
FIG. 2A is an in vitro study of nitrohistidine on Chinese hamster ovary (CHO) cells. CHO cells were in use in an F12 medium with fetal calf serum. A 9 MeV electron beam was used to irradiate the Petri dishes, dose 300 cGy, and a concentration range of 1-4 mM nitrohistidine was employed. In these conditions, nitrohistidine did not appear to possess toxicity by itself, but this did appear to be an effective concentration range for radiosensitization.
Figure 2B:
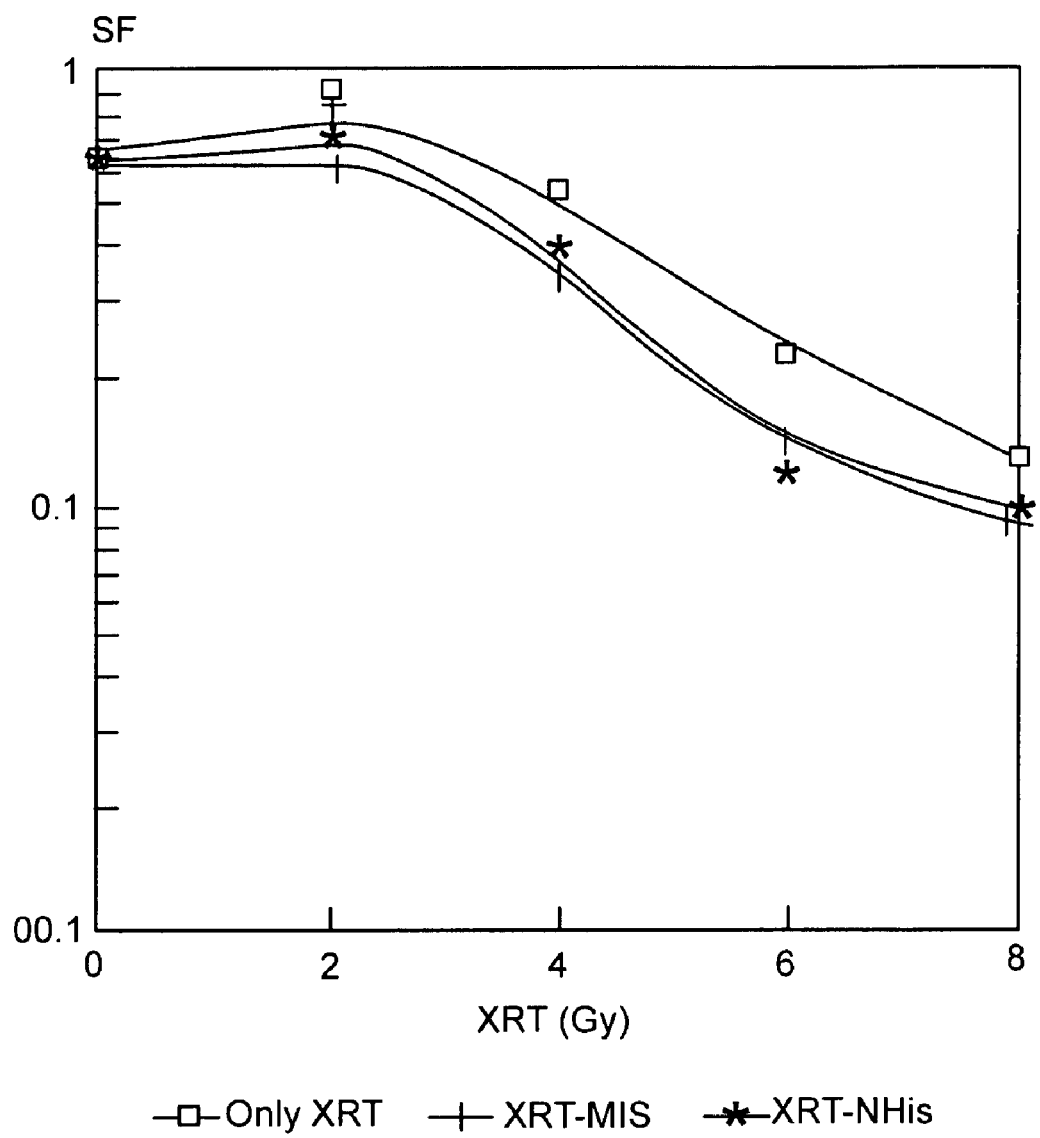
FIG. 2B is an in vitro study of nitrohistidine compared to misonidazole on CHO cells.

An in vitro study using Chinese hamster ovary (CHO) cells was carried out using F12 medium with fetal calf serum for growth of the CHO cells. A 9 MeV electron beam, generated by a Varian Clinac 1800 instrument, was used to irradiate the Petri dishes, at a dose of 300 cGy, and a concentration of 1 to 4 mM 4(5)-nitrohistidine was added alone, or in combination with the radiation dose. Results of this study are shown in FIG. 2A. As can be seen, controls with nitrohistidine alone at all 4 concentrations did not exhibit any toxicity, as seen in the constant levels of cells remaining at all 4 concentrations of nitrohistidine (exhibited along the Y-axis as the S. fraction—SF—the surviving fraction of cells, as a log scale from 10 to 1, with 1 being the number of cells present at time zero). In contrast, in the presence of ionizing radiation (Nitro+XRT) it can be seen that the S. fraction value decreased from just under 1 to just under 0.6 at all four concentrations tested, indicating that this concentration range is an effective concentration range for radiosensitization, and that nitrohistidine may be a promising radiosensitizer for use for cancer treatment in vivo in conjunction with radiation therapy. Additional studies found that 2 mM 4(5)-nitrohistidine was nearly as effective as 5 mM (data not shown), and that in vitro efficacy of 4(5)-nitrohistidine as a radiosensitizer was similar to that of misonidazole when both were administered at 2 mM concentration (See FIG. 2B).

EXAMPLE 2

Figure 3:
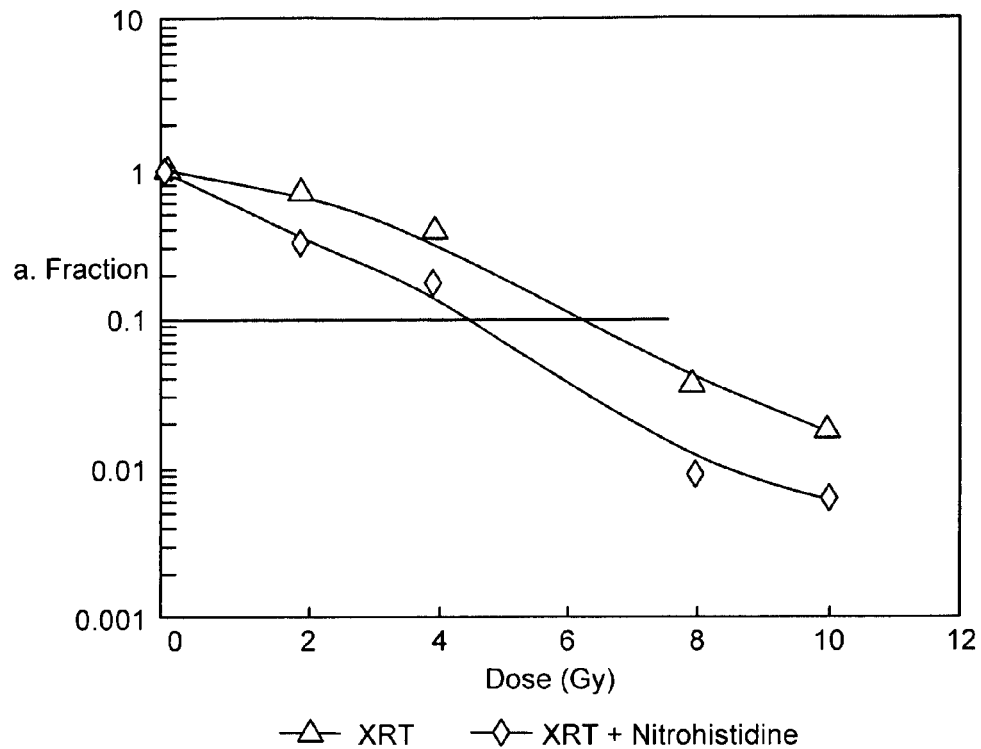
FIG. 3 is an in vitro study of nitrohistidine in CHO cells after pretreatment with hypoxic conditions. In this in vitro assessment of nitrohistidine as a radiosensitizer, CHO cells underwent a 30 minute pre-incubation in hypoxic conditions. The cells exposed to nitrohistidine had 2 mM present. Nine MeV electrons were utilized to deliver the indicated radiation doses. The calculated enhancement ration in this experiment was 1.38 (i.e. the killing power of radiation was multiplied by 1.38).

In Vitro Study of 4(5)-Nitrohistidine as a Radiosensitizer Under Hypoxic Conditions As in Example 1, CHO cells were grown in F12 medium supplemented with fetal calf serum. However, before ionizing radiation treatment, the CHO cells underwent a 30-minute pre-incubation in hypoxic conditions, in the presence or absence of 2 mM 4(5)-nitrohistidine. A 9 MeV electron beam, as in Example 1 above, was used to deliver the radiation doses ranging from 0 to 10 Gy. FIG. 3 shows the S. Fraction plotted against radiation dose, in Gy, at 0, 2, 4, 6, 8, and 10 Gy for radiation alone (XRT, indicated with ✦) and radiation plus 2 mM nitrohistidine (XRT +Nitrohistidine, indicated with ✧).

As can be seen in FIG. 3, the cells exposed to 2 mM 4(5)-nitrohistidine exhibited a radiation dose-dependent depletion of the S. Fraction consistently over that observed with just radiation alone, down to about 0.006 at 10 Gy. The calculated enhancement ratio, at the 0.1 level SF value, equivalent to the killing power of the 4(5)-nitrohistidine plus radiation over treatment with radiation alone (determined using the radiation dosage and radiation plus nitrohistidine dosages required to effect 90% killing of the tumor cells) was determined to be 1.38.

EXAMPLE 3

In vitro Synergism of Buthionine Sulfoximine and 4(5)-Nitrohistidine

Figure 4:
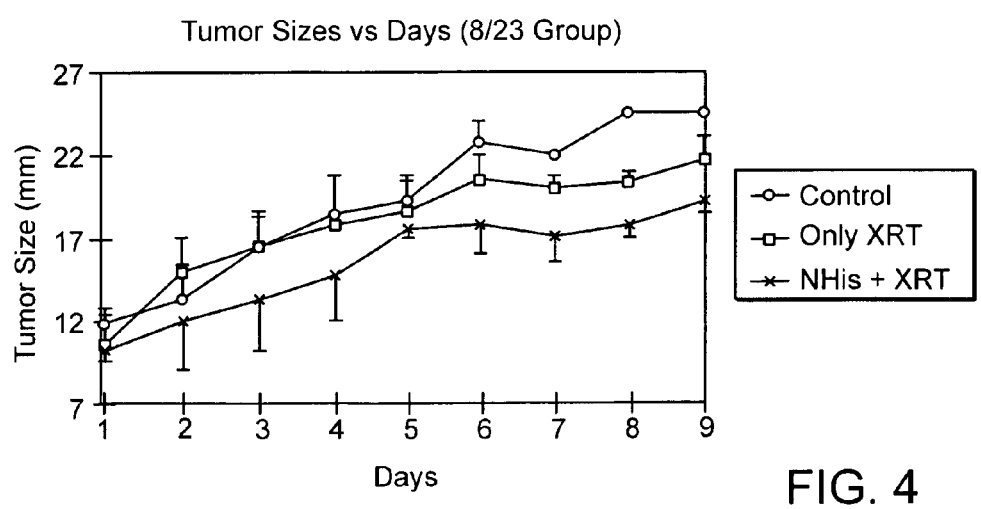
FIG. 4 is an in vivo Growth Retardation Study of Lewis lung carcinoma in rats. Groups of 5-6 mice were subcutaneously implanted with Lewis Lung Carcinoma cells and permitted to grow a small measurable tumor in the hind leg. Radiosensitizers were given by i.p. injection. In some comparative experiments, nitrohistidine was employed at half the concentration of misonidazole. The measurable tumors were treated with a single 500 cGy fraction of 9 MeV electrons.

Chinese hamster ovary cells were grown on F12 medium supplemented with fetal calf serum. Cells were treated with dosages of radiation from 0 to 10 Gy, using a 9 MeV electron beam as above, either alone or in the presence of nitrohistidine, buthionine sulfoximine, or 4(5)-nitrohistidine plus buthionine sulfoximine together. When present, the buthionine sulfoximine and 4(5)-nitrohistidine were added at 2 mM concentration. As can be seen in FIG. 4, results with cells treated with dosages of radiation from 0 to 10 Gy alone (XRT, indicated by ■), or in the presence of 4(5)-nitrohistidine (XRT+NHis, indicated by ▻), buthionine sulfoximine (XRT+BSO, indicated by ✳), or 4(5)-nitrohistidine plus buthionine sulfoximine together (XRT+NHis+BSO, indicated by ⊟) show that the radiation plus NHis plus BSO exhibited an enhanced effect relative to radiation alone or with either the NHis or BSO singly. S. fractions remaining for the combined dual drug/radiation treatment indicate an initial lag time, before continued depletion of cells surviving, down to less than 0.01 SF at 10 Gy in the presence of both NHis and BSO. The enhancement ratio calculated for the combined treatment was greater than two over that of any other treatment combination.

EXAMPLE 4

In Vivo Growth Retardation Experiment 1 with Lewis Lung Carcinoma

Groups of 5-6 mice (C-57) were subcutaneously implanted in the hind leg with Lewis lung carcinoma cells and the cells were permitted to grow until a measurable tumor was evident. Radiosensitizers were administered using i.p. injection at 2 mM concentration, and then treated with a single 500 cGy dose administered with a 9 MeV electron beam and tumor size measured daily for a period of 9 days. Control mice were implanted with tumor cells and left untreated.

Figure 5:
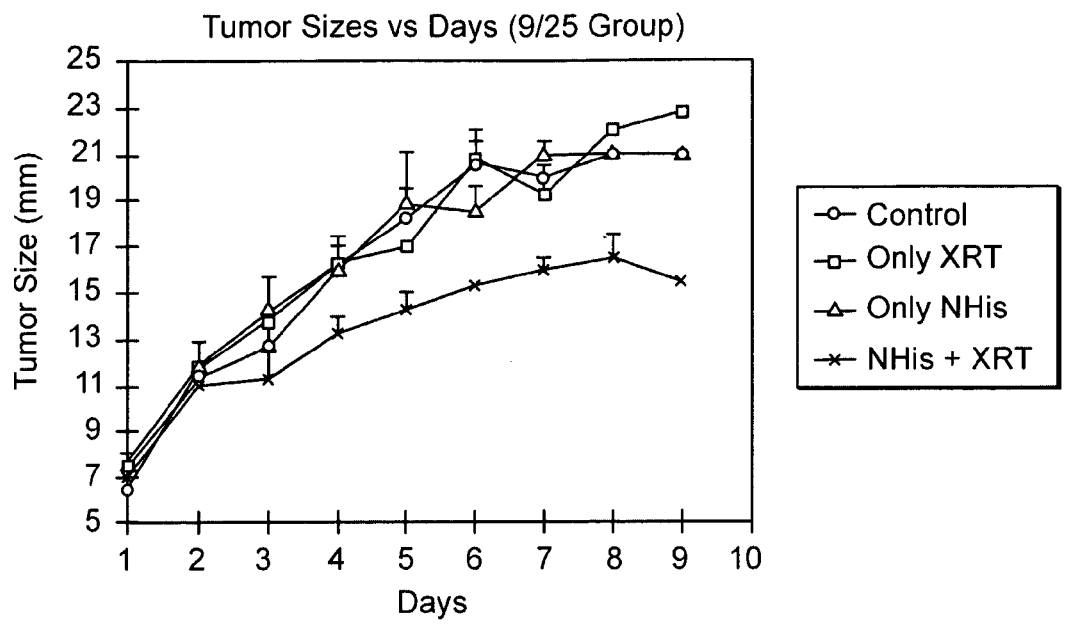
FIG. 5 is a tumor size assessment plot from the Growth Retardation Study of FIG. 4, showing tumor size as a function of time (in days).

As can be seen in FIG. 5, tumor size grew from about 10-12 mm at day I to about 23 mm at day 9 for the control group (indicated by ─○─), to only about 20 mm for the mice treated with radiation alone (XRT, indicated by ─□─) and to only about 18 mm for mice treated with radiation and 4(5)-nitrohistidine (NHis+XRT, indicated by ─■─). This indicates a growth retardation of about 22% compared to the control group, and a growth retardation of about 10% compared to the group treated with radiation alone.

Figure 6:
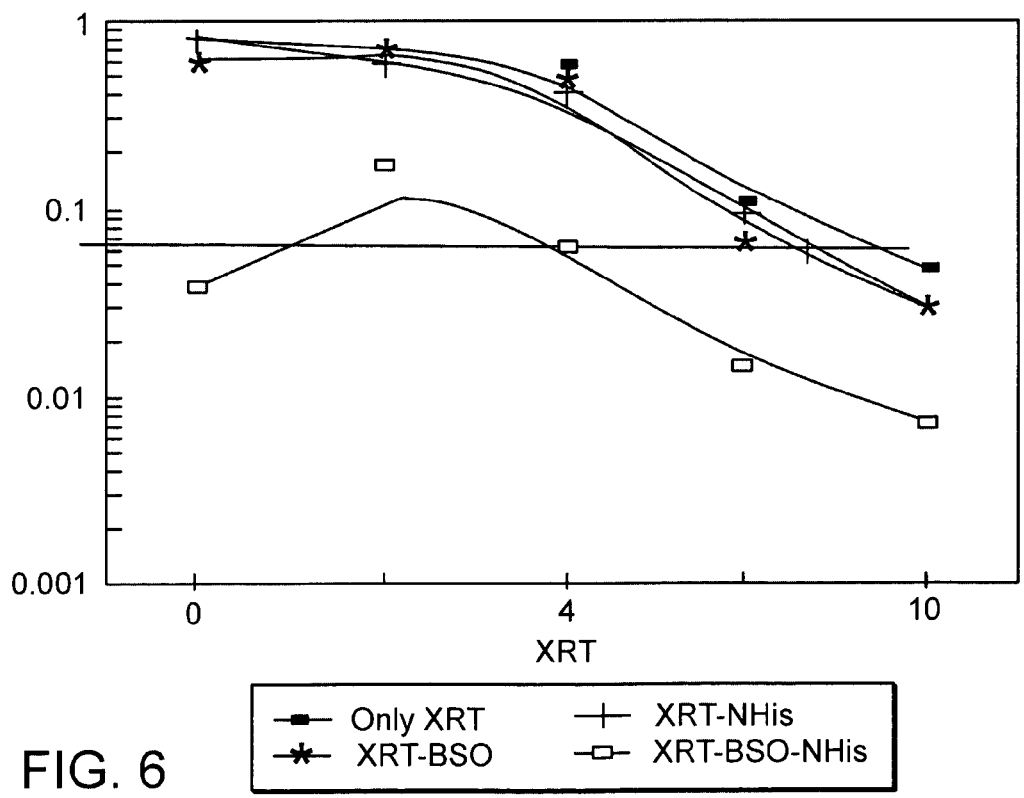
FIG. 6 shows in vitro synergism of buthionine sulfoximine and nitrohistidine as radiosensitizers in CHO cells. Buthionine sulfoximine is an agent known to deplete the levels of endogenous detoxifier and radioprotector glutathione. It has some radiosensitization properties of its own, but here demonstrates a powerful synergism with nitrohistidine. In several experiments, as here, the enhancement ration was greater than two with both agents present. CHO cells were used in the experiments and trhe compounds were present at 2 mM concentration as indicated.

Similar results with a second group of mice are shown in FIG. 6, but in this group, the growth retardation of NHis+XRT is more almost 35% compared to the XRT treatment alone (the tumor was reduced from about 23 mm to about 15 mm at day 9) and about 29% compared to the control or NHis alone (the tumor was reduced from about 21 mm to about 15 mm at day9).

EXAMPLE 5

In Vivo Growth Retardation Experiment 2 with Lewis Lung Carcinoma

Another growth retardation study was done in mice implanted with Lewis lung carcinoma comparing 4(5)-nitrohistidine (NHis) plus radiation treatment to misonidazole plus radiation treatment. In this study, misonidazole plus radiation-treated mice lagged in tumor growth initially, but then grew again parallel to the growth rate of the control mice, indicating that after an initial response, misonidazole plus radiation had no ability to retard tumor growth. In contrast, mice treated with NHis plus radiation showed a plateau in tumor growth after 9-10 days, indicating that tumor growth had effectively ceased. Evidence of this plateau can also be seen in FIG. 5, above.

These results indicate that 4(5)-nitrohistidine plus radiation, in vivo, is a more potent and effective radiosensitizer than misonidazole, presumably due to the concentration of NHis in tumor cells through uptake with the cells' amino acid transport system.

EXAMPLE 6

Intracranial Rat Model Radiosensitizer/Radiotherapy Study

A. Tissue Culture Studies

Rat glioma cell line C6/LacZ is obtained from American Tissue Culture Collection (ATCC). These cells constitutively express the LacZ reporter gene. Cell lines are maintained in Dulbecco's modified Eagle's medium, supplemented with 15% heat-inactivated fetal calf serum and 0.2 mM glutamine, 50 g/mL neomycin, and 100 µg/mL streptomycin. Irradiation of cells is done in the log phase growth, and the cells are then dispersed by trypsinization, suspended in drug-free medium and irradiated in suspension using approximately a 9 MeV electron beam of X-rays generated by a Varian Clinac 1800 instrument at a dose rate of up to approximately 2-10 Gy/min, as required.

After irradiation, cells at each dose level are plated, plates are fixed and stained at about 7 to 9 days after plating, and colonies of >50 cells are scored. Survival curves are fitted to the data points using the linear-quadratic model. For measurement of the effect of incorporation of the nitrohistidine radiosensitizer, cells in exponential growth are cultured for 72 hr before irradiation in medium adjusted to between about $10^{-3}$ to $10^{-5}$ M with respect to the radiosensitizer. Other drugs, such as buthionine sulfoximine, can also be added to the medium at the same time as the radiosensitizer, at 72 hr before irradiation, to examine any possible synergistic effects.

B. In vitro Drug Release

In vitro drug release is measured as described in published reports, such as *Int J Radiat Oncol Bio Phys* (1997) 39: 497-504, the contents of which are incorporated by reference herein. Polymer rods, beads, or matrices containing labeled (i.e., radiolabeled, fluorescence-labeled, etc.) or non-labeled radiosensitizer, and optionally additional drug(s), are placed in phosphate-buffered saline at 37° C. Solutions are collected daily, and fresh phosphate-buffered saline is added to the container, as needed. Solutions are analyzed for radiosensitizer by ultraviolet light, or other means, depending on the nature of the radiosensitizer and whether a label is used to detect the radiosensitizer. These studies are used to help determine appropriate doses and efficacy of potential radiosensitizers and combinations of radiosensitizers with additional agent(s).

C. Intracranial Implant of C6 Tumors

The C6 cell line was developed from a rat glioblastoma induced in randomly bred Wistar rats by N-nitrosomethylurea administration (see *J Neurosurg* (1971) 34:310-323), and transplantation of cultured C6 cells into the brain of rats by a stereotaxic procedure produces intracerebral tumors representing, as close as possible, the characteristics of spontaneous gliomas, with concomitant good reproducibility. Cells cultured as described above, in A, are harvested by trypsinization, pelleted by centrifugation, and resuspended for intracranial implant. For tumor implantation, anesthetized rats are placed in a stereotactic head frame and a small frontal craniectomy is drilled about 2.5 mm from the midline and about 1.0 mm anterior to the bregma. Glioma cells ($5 \times 10^5$/50 µL) are implanted stereotactically to a depth of about 4 mm below the craniectomy, using a Hamilton syringe. The craniectomy is resealed with bone wax and the scalp closed.

D. Radiosensitizer/Polymer Implants

Suitable biodegradable polymer materials include a homopolymer of lactic acid; a homopolymer of glycolic acid; a copolymer of poly-D,L,-lactic acid and glycolic acid; a water-insoluble peptide salt of a luteinizing hormone-releasing hormone (LHRH) analogue; a poly(phosphoester); a bis(p-carboxyphenoxy)propane (CPP) with sebacic acid copolymer; a polyanhydrides polymer; poly(lactide)-co-glycolide)polyethylene glycol copolymers; and an ethylene-vinyl acetate copolymer. The biodegradable polymers are synthesized as described in the literature according to published procedures (see, for example, *J Biomed Mat Res* (1985)19:941-955 (CPP-sebacic acid copolymer); U.S. Pat. No. 6,376,644 (poly (phosphoester)); U.S. Pat. No. 6,699,504 (LHRH analogs); U.S. Pat. No. 6,201,072 (poly(lactide)co-glycolide)polyethylene glycol copolymers); and U.S. Pat. No. 5,792,477 (poly-D,L,-lactic acid and glycolic acid copolymers). Preparations of radiosensitizer-polymer implants are then prepared, according to established procedures. Briefly, the radiosensitizer and polymer are mixed, by grinding or other mechanical means, to create a homogeneous mixture, heated to melt the polymer, and extruded to create rods, beads, or other radiosensitizer-polymer matrix implants, as desired. The radiosensitizer-polymer implants are then cooled, and stored desiccated, until needed.

E. Radiosensitizer Administration

The polymer implants, containing 5-25% wt/wt radiosensitizer and optionally, additional agent, are implanted near the tumor through the original hole where the tumor was implanted, using fine forceps to place the polymer/radiosensitizer implant on top of the site of the tumor implant. Implantation is approximately 8-15 days after tumor implantation, as desired. Implantation can also be done through injection with a syringe, if the polymer matrix is in the appropriate form, for example, microbeads.

F. External Beam Radiotherapy

Rats are anesthetized and tumors irradiated using approximately a 9 MeV electron beam of X-rays generated by a Varian Clinac 1800 instrument at a dose rate of up to approximately 2-10 Gy/min, as required. Single-dose hemibrain radiotherapy is done using a 18-mm diameter circular AP field on day 12-15 after tumor implant, as desired, and 2-3 days after implant of the polymer/radiosensitizer matrix.

G. Tumor Growth Assessment

After tumor implant, rats are examined daily for behavioral and neurological signs of tumor growth. Signs include decreased alertness, passivity, poor grooming, irritability, fearfulness, and neurological deficits such as focal motor deficits and gait disturbance. Animals are killed when 4 of these signs appear, indicating increasing intracranial pressure as the tumor size the behavioral and neurological symptoms worsen. At 14 days, tumor volume will be approximately 20-30 mm$^3$, and at 16-17 days after implant, the earliest at which extraneous signs of tumor growth are typically observed, tumor volume is approximately 30-40 mm$^3$. As the tumor continues to grow, most rats will show symptoms by about 20-23 after implant, and be killed. Rats from all experiments are autopsied at the time of death and the tumor size noted, and the presence of aggressive tumor growth verified.

H. Statistical Analysis

Survival can be plotted in various ways, including on a Kaplan-Meier survival curve, allowing survival data to be compared by a log-rank test. Statistical analysis can then be done using any statistical package software.

EXAMPLE 7

Human Radiosensitizer/Radiotherapy Study in Astrocytomas

A. Tissue Culture Studies

To screen for effective doses and radiosensitizer combinations for potentiation of radiotherapy in human cancers, human cancer cell lines of interest, particularly glioblastomas, obtainable from American Tissue Culture Collection (ATCC) are selected. The various cell lines are maintained in Dulbecco's modified Eagle's medium or an equivalent, supplemented with 10-15% heat-inactivated fetal calf serum, as needed, and 0.2 mM glutamine, 50 g/mL neomycin, and 100 µg/mL streptomycin or other antibiotics, as described for culturing the particular cell line of interest. Irradiation of cells is done in the log phase growth, and the cells are then dispersed by trypsinization, suspended in drug-free medium and irradiated in suspension using approximately a 9 MeV electron beam of X-rays generated by a Varian Clinac 1800 instrument at a dose rate of up to approximately 2-10 Gy/min, as required.

After irradiation, cells at each dose level are plated, plates are fixed and stained at about 7 to 9 days after plating, and colonies of >50 cells are scored. Survival curves are fitted to the data points using the linear-quadratic model. For measurement of the effect of incorporation of the radiosensitizer, cells in exponential growth are cultured for 72 hr before irradiation in medium adjusted to between about $10^{-3}$ to $10^{-5}$ M with respect to the radiosensitizer. Other drugs or agents, such as buthionine sulfoximine, an inhibitor of glutathione and N-(phosphonacetyl)-L-aspartic acid (PALA), an inhibitor of L-aspartate transcarbamylase, or various chemotherapy agents of interest, can also be added to the medium at the same time as the radiosensitizer, at 72 hr before irradiation, to examine any possible synergistic (or adverse) effects.

B. In vitro Radiosensitizer Release

In vitro radiosensitizer release is measured as described in published reports, such as Int J Radiat Oncol Bio Phys (1997) 39: 497-504, the contents of which are incorporated by reference herein. Polymer rods, beads, or matrices containing labeled (i.e., radiolabeled, fluorescence-labeled, etc.) or non-labeled radiosensitizer, and optionally additional drugs/agent(s), are placed in phosphate-buffered saline at 37° C. Solutions are collected daily, and fresh phosphate-buffered saline is added to the container, as needed. Solutions are analyzed for radiosensitizer by ultraviolet light, or other means, depending on the nature of the radiosensitizer and whether a label is used to detect the radiosensitizer. These studies are used to help determine appropriate doses and efficacy of potential radiosensitizers and combinations of radiosensitizers with additional agent(s).

C. Radiosensitizer/Polymer Implants

One means for administering the radiosensitizer formulations in accordance with the present invention is to use suitable biodegradable polymer materials to prepare an implant to be placed surgically at the site of the tumor. Suitable biodegradable polymer materials include a homopolymer of lactic acid; a homopolymer of glycolic acid; a copolymer of poly-D,L,-lactic acid and glycolic acid; a water-insoluble peptide salt of a luteinizing hormone-releasing hormone (LHRH) analogue; a poly(phosphoester); a bis(p-carboxyphenoxy) propane (CPP) with sebacic acid copolymer; a polyanhydrides polymer; poly(lactide)-co-glycolide)polyethylene glycol copolymers; and an ethylene-vinyl acetate copolymer. The biodegradable polymers are synthesized as described in the literature according to published procedures (see, for example, J Biomed Mat Res (1985)19:941-955 (CPP-sebacic acid copolymer); U.S. Pat. No. 6,376,644 (poly(phosphoester)); U.S. Pat. No. 6,699,504 (LHRH analogs); U.S. Pat. No. 6,201,072 (poly(lactide)co-glycolide)polyethylene glycol copolymers); and U.S. Pat. No. 5,792,477 (poly-D,L,-lactic acid and glycolic acid copolymers). Preparations of radiosensitizer-polymer implants are then prepared, according to established procedures. Briefly, the radiosensitizer and polymer are mixed, by grinding, or other mechanical means to create a homogeneous mixture, heated to melt the polymer, and extruded to create rods, beads, or other radiosensitizer-polymer matrix implants, as desired. The radiosensitizer-polymer implants are then cooled, and stored desiccated, until needed.

D. Radiosensitizer Administration

The polymer implants, containing 5-25% wt/wt radiosensitizer and optionally, additional agent, are placed near the tumor, if the tumor is accessible, using endoscope-type injection guns, microinjection, a syringe, or surgical implantation. If the tumor is not accessible, polymer/radiosensitizer implants may be administered by any acceptable and compatible means, depending on the polymer formulation, tumor type and location, and individual patient need. Delivered dosages range from between about 0.5 mM to about 4 mM daily, whether released from a slow-release polymer matrix or administered daily in a standard formulation. Accessibility of the tumor, tumor size and type, and the type of radiosensitizer formulation desired, such as a slow-release formulation that is able to deliver the radiosensitizer over a period of weeks, or a formulation that delivers the radiosensitizer over a period of days or even hours, will determined the choice of the specific polymer material and the appropriate form of the polymer matrix to be used in administering the radiosensitizer, for example, microbeads, rods, etc. The radiosensitizer, and optionally other agents, are administered in a slow-release formulation or other acceptable formulation by any suitable means including oral, intravenous, arterial infusion, intraperitoneal, intramuscular, subcutaneous, surgical, and topical.

E. External Beam Radiotherapy

The subject is anesthetized and tumors irradiated using approximately a 9 MeV electron beam of X-rays generated by a Varian Clinac 1800 instrument at a dose rate of up to approximately 2-10 Gy/min, as required. For brain tumors, single-dose hemibrain radiotherapy is done using a 18-mm diameter circular AP field approximately 1 hour to 2-3 days after implant of the polymer/radiosensitizer matrix, depending on the release formulation used.

F. Tumor Growth/Retardation Assessment

Patients are examined daily for behavioral and neurological signs of tumor regression or growth. Neurological symptoms and signs affecting patients with glioblastomas can be either general or focal, and reflect the location of the tumor. Nonetheless, patients are observed for changes/improvements in the following general symptoms: headaches, nausea and vomiting, personality changes such as irritability, and malaise, changes in mental capacity and concentration ability, and slowing of cognitive function. Focal signs of the tumor are also observed for change/improvement, including hemiparesis, changes in sensory perceptions and visual ability, and aphasia. Other signs that can be observed are increase/decrease in frequency of seizures. Tumor size is also assessed using standard MRI techniques with and without contrast, and CT scans. On CT scans, glioblastomas usually appear as irregularly shaped hypodense lesions with a peripheral ring-like zone of contrast enhancement and a penumbra of cerebral edema.

MRI with and without contrast shows lesions that are typically enhancing ring observed on T1-weighted images and a broad surrounding zone of edema apparent on T2-weighted images. The central hypodense core represents necrosis, the contrast-enhancing ring is composed of highly dense neoplastic cells with abnormal vessels permeable to contrast agents, and the peripheral zone of non-enhancing low attenuation is vasogenic edema containing varying numbers of invasive tumor cells. Several pathological studies have clearly shown that the area of enhancement does not represent the outer tumor border because infiltrating glioma cells can be identified easily within, and occasionally beyond, a 2-cm margin.

Positron emission tomography (PET) scans and magnetic resonance (MR) spectroscopy can be helpful to identify and characterize glioblastomas in difficult cases, such as those associated with radiation necrosis or hemorrhage. On PET scans, increased regional glucose metabolism closely correlates with cellularity and reduced survival. MR spectroscopy demonstrates an increase in the choline-to-creatine peak ratio, an increased lactate peak, and decreased N-acetylaspartate (NAA) peak in areas with glioblastomas. All of these characteristics can be observed for changes/improvements during and after the course of treatment to assess efficacy and indicate whether changes in dosage and/or administration means are indicated.

G. Statistical Analysis

Survival and tumor size can be plotted in various ways, including on a Kaplan-Meier survival curve, allowing survival data to be compared by a log-rank test. Statistical analysis can then be done using any statistical package software.

EXAMPLE 8

Radiosensitizer Potentiation of Radiotherapy in Humans With Glioblastomas, Augmented by Chemotherapy Methods for potentiating cancer radiotherapy treatment using radiosensitizers can also be done with patients that are, or have been, additionally treated with standard chemotherapy. As described in Example 7 above, patients are administered a radiosensitizer formulation and then treated with radiotherapy and chemotherapy regimen.

Carmustine (bischloroethylnitrosourea—i.e. BCNU) and cis-platinum (cisplatin) are the primary chemotherapeutic agents for treatment of malignant gliomas. Data from the University of California at San Francisco indicate that, for the treatment of glioblastomas, surgery followed by radiation therapy leads to 1-, 3-, and 5-year survival rates of 44%, 6%, and 0%, respectively. By comparison, surgery followed by radiation and chemotherapy using nitrosourea-based regimens resulted in 1-, 3-, and 5-year survival rates of 46%, 18%, and 18%, respectively.

In this embodiment, chemotherapy agents can be formulated with the radiosensitizer to be administered in a controlled-release formulation over hours, days, or weeks. Alternatively, the chemotherapy agents may be administered independently of the radiosensitizer using standard chemotherapy formulations and administration routes, such as by i.v. or oral routes.

Tumor size and response to treatment is assessed as described in Example 7 above. For tumors other than glioblastomas, other chemotherapeutic agents routinely used for treatment of such cancers, may be formulated for administration in combination with, or independent from, the radiosensitizer.

What is claimed is:

1. A method of potentiating radiotherapy cancer treatment comprising:
    administering to a patient in need thereof a therapeutically effective amount of a composition comprising a radiosensitizer of formula (I)

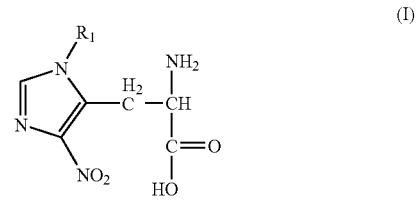

(I)

wherein $R_1$ is H; and
    directing radiotherapy at a prescribed dosage to a locus of cancer,
wherein the cancer is a small cell lung carcinoma or a non small cell lung carcinoma.

2. A method of potentiating radiotherapy cancer treatment according to claim 1, wherein the composition further comprises one or more agents.

3. A method of potentiating radiotherapy cancer treatment according to claim 2, wherein the one or more agents is buthionine sulfoximine, a nitrosourea agent, N-(phosphonylacetyl)-L-aspartic acid (PALA), a chemotherapeutic agent, or any combination thereof.

4. A method of potentiating radiotherapy cancer treatment according to claim 1, further comprising, administering daily doses of the radiosensitizer throughout the course of treatment.

* * * * *